US00PP10890P

United States Patent [19]

Ammerlaan

[11] Patent Number: Plant 10,890

[45] Date of Patent: May 11, 1999

[54] HYBRID TEA ROSE PLANT NAMED 'RUIYEL'

[75] Inventor: P. G. M. Ammerlaan, Schipluiden, Netherlands

[73] Assignee: De Ruiter's Nieuwe Rosen B.V., Pl de Kwakel, Netherlands

[21] Appl. No.: 08/920,789

[22] Filed: Aug. 29, 1997

[51] Int. Cl.[6] ..... A01H 5/00

[52] U.S. Cl. ..... Plt./134

[58] Field of Search ..... Plt./15, 16, 134, Plt./135

[56] References Cited

U.S. PATENT DOCUMENTS

P.P. 9,421 1/1996 Pouw ..... Plt./14

*Primary Examiner*—Howard J. Locker

*Attorney, Agent, or Firm*—Christie, Parker & Hale, LLP

[57] ABSTRACT

A new variety of Hybrid Tea rose plant producing yellow flowers of good form and suitable for growing under glass.

1 Drawing Sheet

BACKGROUND OF THE INVENTION

The present invention relates to a new and distinct variety of rose plant of the hybrid tea rose class which was discovered as a natural mutation in a controlled planting of 'Ruicrevi' U.S. Plant pat. No. 9,421 in Schipluiden, The Netherlands. The varietal denomination of the new variety is 'Ruiyel'. The new variety was isolated and asexually reproduced by budding in The Netherlands.

SUMMARY OF THE INVENTION

Among the novel characteristics possessed by this new variety which distinguish it from its parent and all other varieties of which I am aware are its attractive yellow flowers of good form and long stems borne on a floriferous plant and suitable for production of cut flowers under glass. The new variety has been reproduced through propagation by cuttings, grafting, budding and micropropagation.

Asexual reproduction by budding of the new variety as performed in De Kwakel, Holland, shows that the foregoing and other distinguishing characteristics come true to form and are established and transmitted through succeeding propagations.

Comparison With Parent

The new variety differs from its parent in flower color. The color of 'Ruiyel' is deep yellow in contrast to lighter, less intense, yellow color of 'Ruicrevi'.

BRIEF DESCRIPTION OF ILLUSTRATION

The accompanying illustration shows a typical specimen of the vegetative growth and flowers of the new variety depicted in color as nearly true as it is reasonably possible to make the same in a color illustration of this character.

DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart. Phenotypic expression may vary depending upon growing conditions under different climate, soil, and cultivation conditions.

Parentage: Mutation of 'Ruicrevi'.
Class: Hybrid Tea.

The following further horticultural description is based on observations made of specimens grown under glass in De Kwakel, Holland.

Flower

Blooming habit: Nearly continuous, in The Netherlands under glass about 150 stems/m$^2$/year.

A. Bud:
- (1)*Size.*—Medium, about 2 to 2.5 inches long and about 1 to 1.5 inches wide.
- (2) *Form.*—Ovate (shape of longitudinal section just before separation of sepals); urn-shaped after sepals part.
- (3) *Color.*—As sepals divide, near 19B.
- (4) *Sepals.*—About same length as bud showing color; top surface near 138C to 138D; undersurface near 137B to 137C; some foliacious.
- (5) *Peduncle.*—Long: Strength-erect, strong. Color near 147A, about 3½ inches in length, few hairs or prickles.

B. Flower: Medium; viewed from above — star-shaped; viewed from side — (a) upper part of fully opened flower, flattened convex; (b) lower part of fully opened flower, flat.
- (1) *Size.*—Average size when fully expanded — about 5 inches.
- (2) *Borne.*—Singly, one to a stem.
- (3) *Form.*—Pointed center, spiral imbricated, outer petals reflex to points.
- (4) *Petalage.*—Fully double, about 25.
- (5) *Color.*—After sepals part and petals unfurl color of petal top surface appears near 20C to 20D; with inner petals (½ to full open) near 20B; petal undersurface near 19D to 20D on outer petals and near 19B on inner petals; overall tonality from a distance is attractive yellow coloration.
- (6) *Peduncle.*—Smooth.
- (7) *Fragrance.*—Weak to medium fruity.
- (8) *Length of stems.*—About 30 inches.

Petals:

(1) *Texture.*—Crisp.

(2) *Appearance.*—Inside velvety and outside satiny.

(3) *Form and size.*—Broad, medium undulation of margin.

(4) *Arrangement.*—Regularly arranged, imbricated.

(5) *Petaloids.*—About 5, crinkled, same color as petals.

(6) *Lasting quality.*—About 14 days on plant, about 10 days after cutting.

Reproductive Organs

A. Stamens, filaments and anthers:

*Arrangement and color.*—Regularly arranged around styles; color of filaments — yellow.

B. Pollen:

*Color.*—Near 21C to 21D.

C. Styles: Long, stigma above mouth of receptacle, yellow.

D. Stigmas: Red, near 44A to 45A, positioned below anthers.

E. Hip: Pitcher-shaped; medium seed vessel at petal fall.

Plant

A. Form: Narrow, bushy, height about 1.8 m, spread about 0.8 m.

B. Growth: Vigorous, average disease resistance.

C. Foliage: Compound 3, 5 and 7 leaflets.

(1) *Size.*—Medium to large width and length.

(2) *Quantity.*—Abundant.

(3) *Color.*—Juvenile foliage — bronze to reddish brown; upper side near 185A to 187A, under side near 184A; medium anthocyanin coloration, (shoot about 8 inches long); mature leaf color — upper side near 136A, under side near 138 A to 138 B.

(4) *Shape.*—Broad oval.

(5) *Texture.*—Upper side is medium glossy; underside is matte.

(6) *Edge.*—Serrate.

(7) *Serration.*—Ordinary, acuminate apices.

(8) *Leaf Stem.*—Color — near 136B.

(9) *Stipules.*—Short, simple, medium green.

(10) *Leaflets.*—Cross section — slight convex; weak undulation of margin; terminal leaflet — medium length; blade about 2 to 3 inches long and 2 to 2.5 inches wide, rounded base.

D. Wood:

(1) *New wood.*—Color — young shoots have weak to medium anthocyanin; coloration — bronze red purple to reddish brown.

(2) *Old wood.*—Color — near 136B.

E. Prickles (thorns):

(1) *Prickles.*—Present; quantity (main stalk) — ordinary; shape of lower side — concave; Length — short prickles absent or very few, long prickles few to medium; Color — near 173C; Position — irregular.

What is claimed is:

1. A new and distinct rose plant of the variety substantially as shown and described.

* * * * *

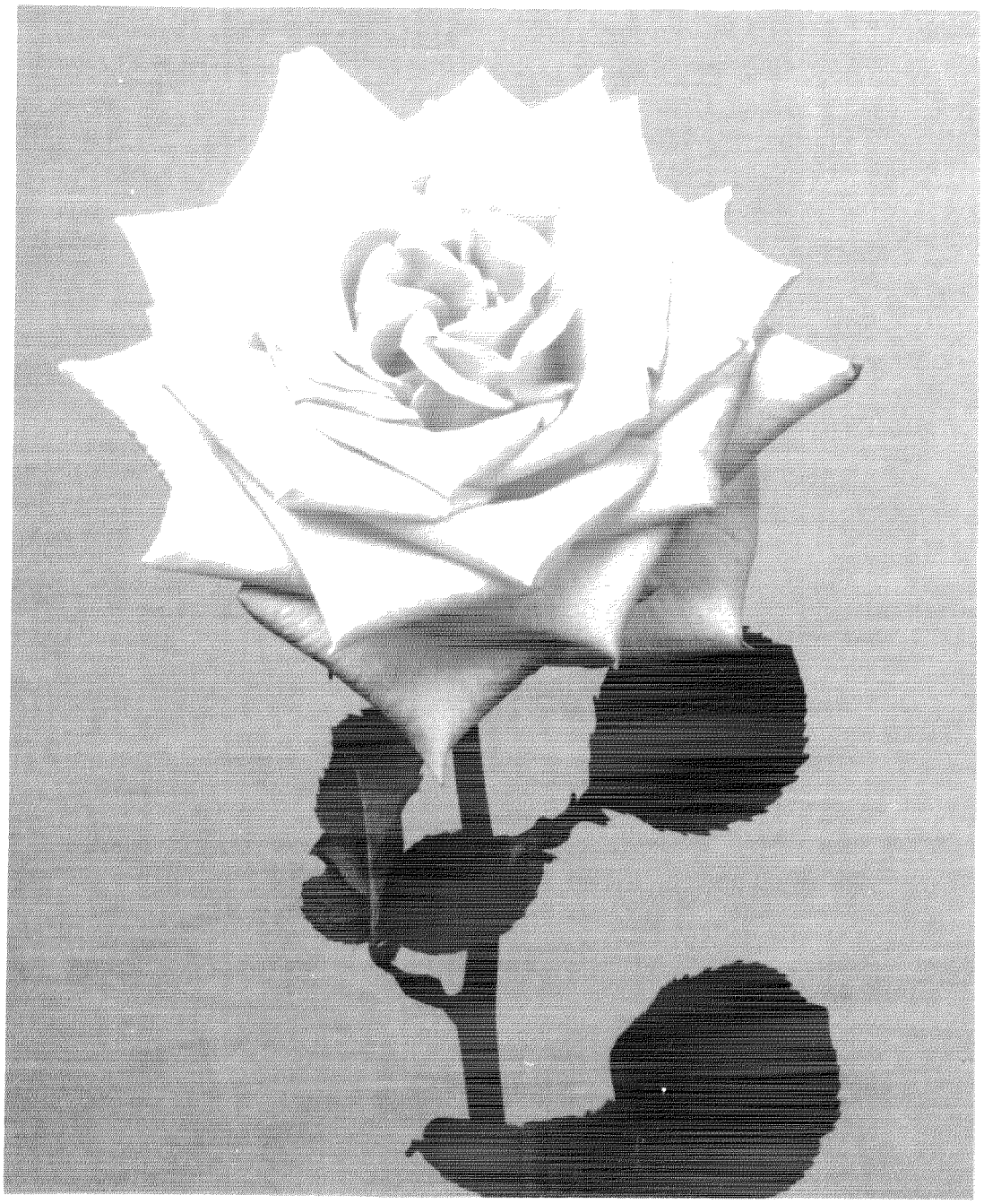

UNITED STATES PATENT AND TRADEMARK OFFICE

CERTIFICATE OF CORRECTION

PATENT NO. : PP 10,890
DATED : May 11, 1999
INVENTOR(S) : P.G.M. Ammerlaan

It is certified that error appears in the above-identified patent and that said Letters Patent is hereby corrected as shown below:

Title page,
Item [22], Filed:, replace "Aug. 29, 1997" with -- Aug. 28, 1997 --.

Column 1,
Line 6, replace "U.S. Plant pat. No. 9,421" with -- U.S. Plant Pat. No. 9,421 --.

Column 2,
Line 25, after "(5) *Peduncle.*—" delete "Long:".

Signed and Sealed this

Eighteenth Day of December, 2001

*Attest:*

*Attesting Officer*

JAMES E. ROGAN
*Director of the United States Patent and Trademark Office*